United States Patent [19]

Yum et al.

[11] Patent Number: 4,913,702
[45] Date of Patent: Apr. 3, 1990

[54] FLUID IMBIBING PUMP WITH CATHETER

[75] Inventors: Su I. Yum, Los Altos; Hans H. Balkie, Mountain View, both of Calif.

[73] Assignee: Alza Corporation, Palo Alto, Calif.

[21] Appl. No.: 232,045

[22] Filed: Aug. 15, 1988

[51] Int. Cl.⁴ .............................................. A61M 5/00
[52] U.S. Cl. ................................................... 604/131
[58] Field of Search ............... 604/131, 132, 151, 153, 604/51, 52, 53, 93

Primary Examiner—John D. Yasko
Attorney, Agent, or Firm—D. Byron Miller; Steven F. Stone; Edward L. Mandell

[57] ABSTRACT

An agent dispenser of the fluid imbibing type wherein the dispenser has a closure, such as a plug, closing an open end of the dispenser. The closure has a catheter coupled with it, and the catheter is in agent communication with the interior of the agent receiving means of the dispenser when the closure is put into place in closing relationship to the dispenser. Thus, when the agent receiving portion (reservoir) of the agent receiving means is filled, such as by a needle passing through a septum at the outer end of the closure, not only will the reservoir be filled, but also the catheter will be filled and thereby be primed, so that the catheter will be ready for use after it has been completely primed. The present invention, therefore, permits the filling of the reservoir and the priming of the catheter in a single step.

9 Claims, 1 Drawing Sheet

FLUID IMBIBING PUMP WITH CATHETER

BACKGROUND OF THE INVENTION

1. Field of the Invention

This invention relates to agent dispensers of the fluid imbibing type such as those which are driven osmotically and, more particularly, to an agent dispenser having a catheter which can be preprimed to facilitate the application of a drug or other fluid to a body part.

Fluid imbibing osmotic agent dispensers or pumps are described in U.S. Pat. Nos. 3,760,984; 3,987,790; 3,995,631; 4,034,756; 4,474,575 and 4,539,004; all of which are incorporated herein by reference. The type of agent dispenser set forth in these disclosures includes an inner agent receiving means such as a flexible bag that holds a flowable agent to be dispensed, an intermediate fluid imbibing means such as a layer of osmotically effective solute composition, for example an inorganic salt surrounding the bag, and an outer casing having a portion that is permeable to fluid such as water and surrounds both the bag and the layer of solute composition. The bag has a discharge port which allows the agent to be directed to a location of use.

Actuation of the agent dispenser of the type described is achieved by filling the bag with a flowable agent to be dispensed, then placing the dispenser in an environment, such as in a body cavity or on the skin of a patient. Fluid, typically water is imbibed from the environment by the solute composition through the membrane and into the space between the inner bag and the membrane. The imbibed fluid squeezes the bag, thereby collapsing it and displacing the agent out of the bag through the discharge port provided therefor.

A catheter is often used with an agent dispenser of the type described. To use such a catheter requires that a relatively large number of steps be performed to place the agent dispenser in readiness for applying an agent to the human or animal body. Such steps include attaching the catheter to the filled dispenser, filling the catheter, inserting a flow moderator in the dispenser, removing a flow or moderator cap, and connecting one end of the filled catheter to the dispenser and the other end to the point of use. All of the foregoing steps require time and effort, and it is desirable to minimize the time and effort, if at all possible. Thus, a need exists for improvements in the use of an agent dispenser having a catheter and the present invention which fulfills this need.

2. DEFINITION OF TERMS

The expression "agent" as used herein denotes any drug or agent administered to produce a nutritional, therapeutic or other desired effect including for example: composition in any way affecting any biological entity; substance having a nutrient or stimulating action, or growth inhibiting, destroying or any regulating action on plant growth, controlled or otherwise; substance to be assimilated by any organism, e.g., human being, animal, or lower order organism, for its nourishment or for regulating its growth; substance exhibiting any of the above activities to be directly applied to the habitat, surroundings or environment of any of the above organisms; and substance having any other effect on any other environment, especially any aqueous environment.

Therefore, suitable agents for use with the dispenser of this invention include, without limitation, those which are generally capable of:

1. Preventing, alleviating, treating or curing abnormal or pathological conditions of the living body by such means as destroying a parasitic organism or limiting the effect of the disease of abnormality by chemically altering the physiology of the host or parasite.

2. Maintaining, increasing, decreasing, limiting or destroying a physiologic body or plant function, e.g., vitamin compositions, sex sterilants, fertility inhibitors, fertility promotors, growth promotors, and the like;

3. Diagnosing a physiological condition or state;

4. Controlling or protecting an environment or living body by attracting, disabling, inhibiting, killing, modifying, repelling or retarding an animal or microorganism, such as food and non-food baits, attractants and lures, biocides, pesticides, algicides, parasiticides, rodenticides, insecticides, fungicides, and the like;

5. Preserving, disinfecting or sterilizing; and

6. Controlling or affecting generically an environment, as by introducing a catalyst or metering a reactant into a reacting chemical system, or by effecting any chemical process therein, such as a fermentation, including propagation and/or attenuation of a microorganism.

The term "environment" as used herein denotes any prospective situs for the dispenser of this invention, or at least for the external fluid permeable membrane component thereof, which is comprised of or will provide sufficient fluid, e.g. water, for absorption into the dispenser to develop the needed osmotic pressure on which its motive force depends; and implicit in the foregoing definition of "agent" - one that will develop its action in the presence of such an environment, or one that will develop its action on a remote and/or another environment, which need not be fluid or aqueous.

SUMMARY OF THE INVENTION

The present invention is directed to an agent dispenser of the fluid imbibing type wherein the dispenser has a closure, such as a plug, closing an open end of the dispenser. The closure has a catheter coupled with it, and the catheter is in agent communication with the interior of the agent receiving means when the closure is put into place in closing relationship to the dispenser. Thus, when the reservoir of the agent receiving means is filled, such as by a needle passing through a septum at the outer end of the closure, not only will the reservoir be filled, but also the catheter will be filled and thereby be primed, so that the catheter will be ready for use after it has been completely primed.

The present invention, therefore, permits the filling of the reservoir and the priming of the catheter in a single step. Thus, this feature eliminates the relatively numerous steps required to prime the catheter of a conventional flowable agent dispenser. The dispenser of the present invention is simple and rugged in construction and is economical to assemble and fill.

The primary object of the present invention is to provide an improved osmotic agent dispenser which has a catheter thereon in agent communication with the agent receiving reservoir of the dispenser so that, as the reservoir itself is being filled with the agent to be dispensed, the catheter can be automatically primed so that the dispenser is immediately ready for use after a simple one-step filling operation.

Other objects of this invention will become apparent as the following specification progresses, reference being had to the accompanying drawings for an illustration of the invention.

DETAILED DESCRIPTION OF THE INVENTION

Figure 1:
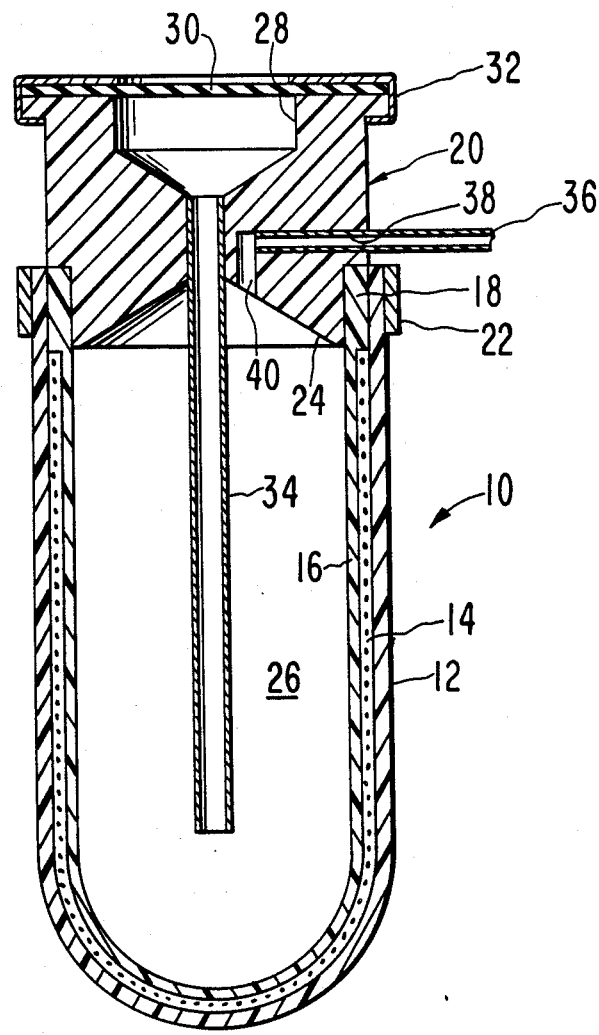
FIG. 1 is a vertical section through the agent dispenser of the present invention, showing the catheter associated with the dispenser.
Figure 2:
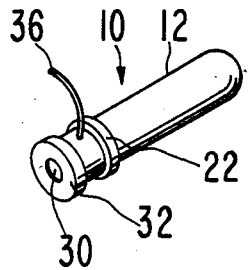
FIG. 2 is a perspective view, on a reduced scale, of the agent dispenser of FIG. 1.

A fluid imbibing dispenser of the present invention is broadly denoted by the numeral 10 and includes an outer, rigid, shaperetaining, casing 12 in the form of a tube, at least a portion of which is a semi-permeable membrane; an intermediate, fluid imbibing means such as osmotically active sleeve 14; and an inner agent receiving means 16. The agent to be dispensed is in a flowable form, preferably in a gel, paste or other semi-solid state, albeit a solution or concentrated solution of agent will sometimes suffice.

The fluid imbibing agent dispenser 10 in which components 12, 14 and 16 form a part is of the type described in commonly owned U.S. Pat. Nos. 3,987,790; 3,995,631 and 4,034,756. In such dispensers, the agent receiving means 16 can be a collapsible bag.

Bag 16 and casing (membrane) 12 have open, outer ends as shown in FIG. 1. Bag 16 has a lateral flange 18 thereon which abuts the inner surface at the outer end of membrane 12. The lateral thickness or length of flange 18 is equal to the thickness of sleeve 14 in its unactuated condition so that the interface between flange 18 and the inner surface of membrane 12 presents a seal preventing the discharge of solute composition from sleeve 14.

A closure in the form of a plug 20 is inserted in the open end of bag 16 in closing relationship thereto. Plug 20 is of resilient material, such as rubber, or hard material, such as plastic or the like and it withstands the compression force exerted by the outer end of bag 16 when a compression band 22 is wrapped around the outer surface of the outer end of membrane 12 as shown in FIG. 1. Thus, the interface 24 between plug 20 and bag 16 provides an effective seal against flow of agent in the reservoir 26 of bag 16 outwardly of the dispenser.

The outer end of plug 20 is provided with a central recess 28 which is covered by a rubber septum 30 which is held in place by a metal cap 32. A tube 34 is inserted through plug 20 centrally thereof and places recess 28 in agent communication with reservoir 26, which is the agent receiving portion of the agent receiving means. Sleeve 14 is a fluid imbibing means for forcing the agent from the agent receiving means. Sleeve 14 can be an osmotically effective solute composition therein, such as an inorganic salt.

A catheter 36 is coupled with a bore 38 extending from the side of plug 20 to an internal recess 40 within the plug, recess 40 being open at the inner end thereof so as to place the reservoir 26 in agent communication with the interior of catheter 36. The outer end of the catheter has an hypodermic needle associated therewith for application of an agent in the dispenser to a point of use. In the alternative, the outer end of the catheter could be capped so that a needle can be attached to the outer end of the catheter when the cap is removed.

To fill dispenser 10, a needle pierces septum 30 and enters recess 28. An agent from a source flows toward and is injected into reservoir 26 through tube 34. As the agent fills the reservoir 26, it overflows the reservoir and passes into recess 40 and then into catheter 36 to prime the catheter and make it ready for immediate use after it has been primed.

Figure 3:
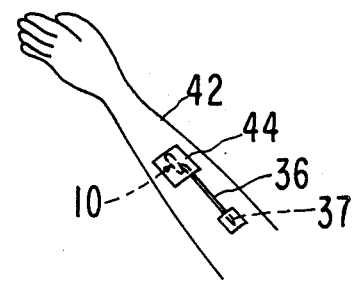
FIG. 3 is a schematic view of an arm of a patient, showing the way in which the agent dispenser is used to inject a flowable agent from the dispenser into the patient.

In use, dispenser 10 is, for instance, placed on a body part, such as the arm (FIG. 3), of a patient to be treated with the agent in the dispenser. Dispenser 10 is held in place by an occlusive cover 44 which can be moistened to provide an aqueous environment for membrane 12 of dispenser 10. Catheter 36 with needle 37 on the outer end thereof extends outwardly from dispenser 10 and the needle is inserted into a vein of the patient. When so located, dispenser 10 operates to cause water to be imbibed from the environment adjacent to cover 44, the water being imbibed because of the solute composition in sleeve 14. The water imbibed through the membrane and into the sleeve causes bag 16 to be squeezed and collapsed to force the agent in reservoir 26 out of the reservoir through recess 40 and through preprimed catheter 36 into the patient through needle 37.

Dispenser 10, therefore, provides a simple osmotic pump having a catheter which is pre-primed when the dispenser itself is provided with an agent to be dispensed. Thus, dispenser 10 allows the simplification of filling of the dispenser reservoir 26 while still providing a construction which is simple and rugged and which is inexpensive to produce.

Having thus generally described our invention and having provided specific embodiments thereof, it will be readily apparent to workers skilled in the art that various modifications and substitutions can be made without departing from the scope of this invention which is limited only by the following claims.

What is claimed is:

1. An agent dispenser comprising, in combination:
   an outer, generally rigid casing at least a portion of which is a semipermeable membrane;
   agent receiving means within said casing for receiving the agent to be dispensed;
   a fluid imbibing means for forcing said agent from said agent receiving means;
   a catheter; and
   means for coupling the catheter to the agent receiving means with the catheter being in agent communication with the agent receiving portion of said agent receiving means, said coupling means including a resilient plug having an inner surface and provided with a recess extending into the plug from said surface thereof, said catheter extending through the plug and having an open end in agent communication with the recess, whereby the catheter can be filled as the agent receiving means is filled.

2. The agent dispenser as set forth in claim 1, wherein said agent receiving means includes a flexible bag having a reservoir, said plug having an outer surface and a second recess in the outer surface thereof, there being a passage through the plug for placing the second recess in agent communication with the reservoir of the bag when the plug covers an open end of the bag.

3. The agent dispenser as set forth in claim 2, wherein said plug has a resilient septum covering the second recess.

4. The agent dispenser as set forth in claim 3, wherein the plug has a side surface, and catheter projecting into the plug from said surface and having an open, inner end in agent communication with the interior of the bag.

5. An agent dispenser comprising in combination:
an outer, generally rigid casing at least a portion of which is a semipermeable membrane;
an inner collapsible bag within the casing and adapted to contain an agent to be dispensed, said bag having an open outer end;
a fluid imbibing composition between the membrane and the bag, there being a closure for closing the open end of the bag, said closure having means for directing the agent to be dispensed into the bag; and
a catheter coupled to the closure and being in agent communication with the interior of said bag, whereby the catheter can be filled as the bag is filled.

6. The agent dispenser as set forth in claim 5, wherein said closure includes a resilient plug having an inner surface and provided with a recess extending into the plug from said surface thereof, said catheter extending through the plug and having an open end in agent communication with the recess.

7. The agent dispenser as set forth in claim 6, wherein said plug has an outer surface and a second recess in the outer surface thereof, there being a passage through the plug for placing the second recess in agent communication with the interior of the bag.

8. The agent dispenser as set forth in claim 7, wherein said plug has a resilient septum covering the second recess.

9. The agent dispenser as set forth in claim 7, wherein the plug has a side surface, said catheter projecting into the plug from said surface and having an open, inner end in agent communication with the interior of the bag.

* * * * *